United States Patent
Bui et al.

(10) Patent No.: US 10,898,264 B2
(45) Date of Patent: Jan. 26, 2021

(54) DOUBLE LOOP LASSO WITH SINGLE PULLER WIRE FOR BI-DIRECTIONAL ACTUATION

(71) Applicant: BIOSENSE WEBSTER (ISRAEL) LTD., Yokneam (IL)

(72) Inventors: Julie Bui, Rosemead, CA (US); Oscar Galvan, Covina, CA (US); Jose Jimenez, Ontario, CA (US); Thanh Nguyen, El Monte, CA (US); Ricardo Padilla, Tustin, CA (US); Thomas V. Selkee, Claremont, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 16/695,165

(22) Filed: Nov. 25, 2019

(65) Prior Publication Data

US 2020/0093540 A1    Mar. 26, 2020

Related U.S. Application Data

(63) Continuation of application No. 15/925,557, filed on Mar. 19, 2018, now Pat. No. 10,485,610, which is a
(Continued)

(51) Int. Cl.
| | | |
|---|---|---|
| *A61B 5/042* | (2006.01) | |
| *A61B 18/14* | (2006.01) | |
| *A61B 5/00* | (2006.01) | |
| *A61M 25/01* | (2006.01) | |
| *A61B 5/06* | (2006.01) | |
| *A61M 25/06* | (2006.01) | |

(Continued)

(52) U.S. Cl.
CPC .......... *A61B 18/1492* (2013.01); *A61B 5/042* (2013.01); *A61B 5/0422* (2013.01);
(Continued)

(58) Field of Classification Search
CPC ..... A61B 5/042; A61B 5/6856; A61B 5/6857; A61B 18/1492
See application file for complete search history.

(56) References Cited

U.S. PATENT DOCUMENTS

| 5,626,136 A | 5/1997 | Webster, Jr. |
| 5,807,249 A | 9/1998 | Qin et al. |
| (Continued) | | |

FOREIGN PATENT DOCUMENTS

| CN | 101584905 A | 11/2009 |
| EP | 1072281 A1 | 1/2001 |
| (Continued) | | |

OTHER PUBLICATIONS

Extended European Search Report for European Application No. 13199532.6, dated Apr. 3, 2014, 6 pages.

*Primary Examiner* — Lee S Cohen
(74) *Attorney, Agent, or Firm* — Etan S. Chatlynne; Roberts Calderon Safran & Cole P.C.

(57) ABSTRACT

A catheter has a distal assembly with at least one loop with ring electrodes. A single continuous puller wire for bidirectional deflection is pre-bent into two long portions and a U-shape bend therebetween. The U-shape bend is anchored at a distal end of a deflectable section which is reinforced by at least one washer having at least two holes, each hole axially aligned with a respective lumen in the deflectable section. Each hole is centered with a lumen so that each puller wire portion therethrough is straight and subjected to tensile force only. A proximal end of the support member is flattened and serrated to provide a better bonding to the distal end of the deflectable section.

20 Claims, 7 Drawing Sheets

Related U.S. Application Data continuation of application No. 15/144,705, filed on May 2, 2016, now Pat. No. 9,918,791, which is a continuation of application No. 14/733,833, filed on Jun. 8, 2015, now Pat. No. 9,326,818, which is a continuation of application No. 13/732,283, filed on Dec. 31, 2012, now Pat. No. 9,050,010.

(51) Int. Cl.
*A61B 34/20* (2016.01)
*A61B 18/00* (2006.01)

(52) U.S. Cl.
CPC ............ *A61B 5/065* (2013.01); *A61B 5/4836* (2013.01); *A61B 5/6856* (2013.01); *A61B 5/6857* (2013.01); *A61B 18/1402* (2013.01); *A61M 25/0136* (2013.01); *A61M 25/0147* (2013.01); *A61M 25/0662* (2013.01); *A61B 2018/0016* (2013.01); *A61B 2018/00351* (2013.01); *A61B 2018/00577* (2013.01); *A61B 2018/00839* (2013.01); *A61B 2018/1407* (2013.01); *A61B 2018/1435* (2013.01); *A61B 2018/1465* (2013.01); *A61B 2018/1467* (2013.01); *A61B 2034/2051* (2016.02); *A61B 2562/0209* (2013.01); *A61M 25/0152* (2013.01); *A61M 2025/015* (2013.01); *A61M 2025/0681* (2013.01)

(56) References Cited

U.S. PATENT DOCUMENTS

| | | | |
|---|---|---|---|
| 5,964,757 A | 10/1999 | Ponzi | |
| 6,123,699 A | 9/2000 | Webster, Jr. | |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,267,746 B1 | 7/2001 | Bumbalough | |
| 6,500,167 B1 | 12/2002 | Webster, Jr. | |
| 6,522,933 B2 | 2/2003 | Nguyen | |
| 6,547,757 B1 | 4/2003 | Kranz et al. | |
| 6,628,976 B1 | 9/2003 | Fuimaono et al. | |
| 6,795,721 B2 | 9/2004 | Coleman et al. | |
| 7,187,963 B2 | 3/2007 | Coleman et al. | |
| 7,588,555 B2 | 9/2009 | Pudelko et al. | |
| 7,591,799 B2 | 9/2009 | Selkee | |
| 8,007,463 B2 | 8/2011 | Pudelko et al. | |
| 9,050,010 B2 | 6/2015 | Bui et al. | |
| 9,326,818 B2 | 5/2016 | Bui et al. | |
| 9,918,791 B2 | 3/2018 | Bui et al. | |
| 2001/0025134 A1 | 9/2001 | Bon et al. | |
| 2002/0143378 A1 | 10/2002 | Nguyen | |
| 2002/0165441 A1 | 11/2002 | Coleman et al. | |
| 2003/0181855 A1 | 9/2003 | Simpson et al. | |
| 2005/0107737 A1 | 5/2005 | McDaniel | |
| 2012/0116200 A1 | 5/2012 | Roy et al. | |
| 2012/0157915 A1 | 6/2012 | Hastings et al. | |
| 2013/0085492 A1 | 4/2013 | Plascencia, Jr. et al. | |

FOREIGN PATENT DOCUMENTS

| | | |
|---|---|---|
| EP | 1532999 A2 | 5/2005 |
| JP | H05115426 A | 5/1993 |
| JP | 2003319915 A | 11/2003 |
| JP | 5115426 B2 | 1/2013 |
| RU | 2006118345 A | 12/2007 |
| WO | 9605758 A1 | 2/1996 |
| WO | 2005048858 A1 | 6/2005 |

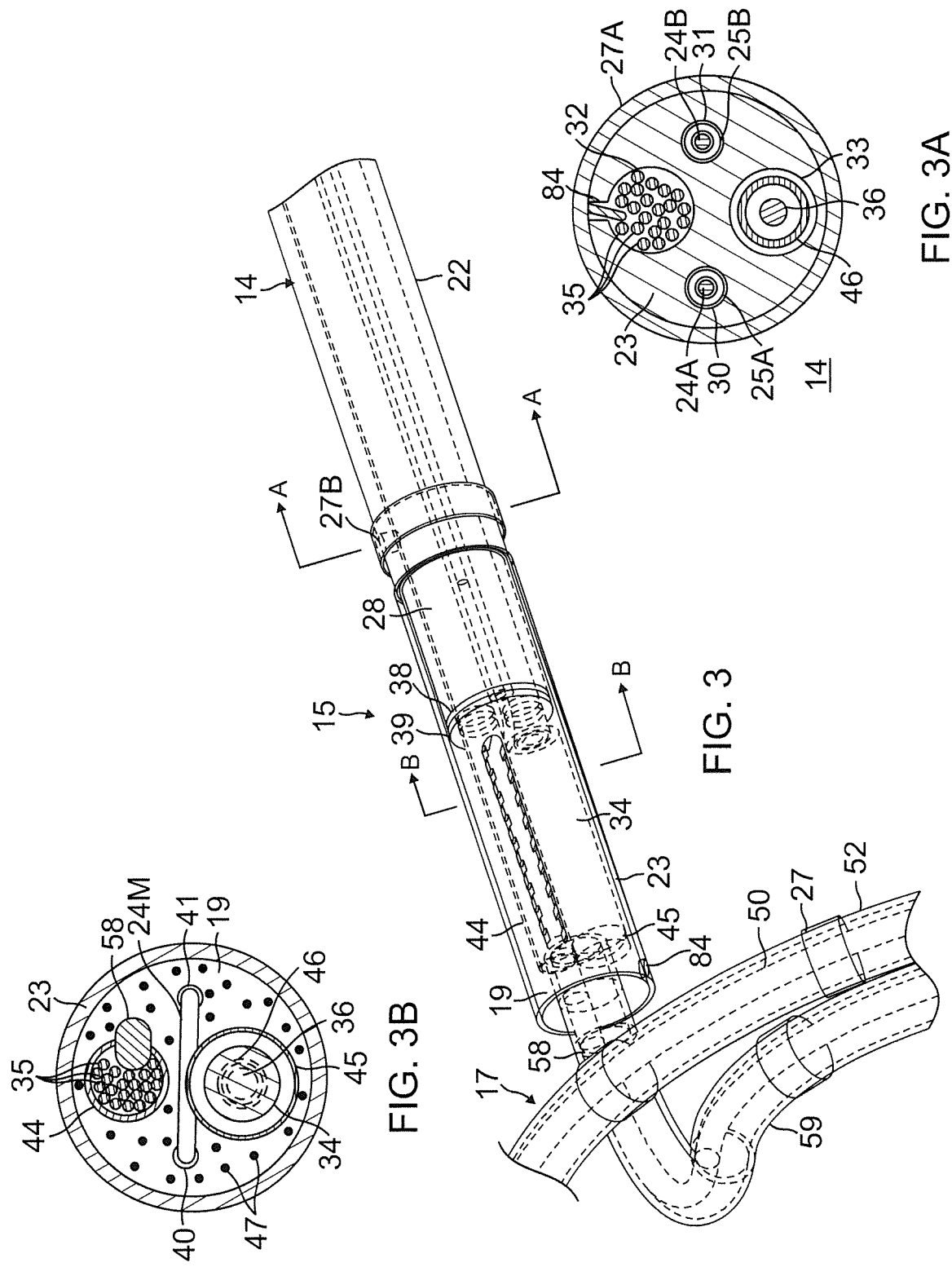

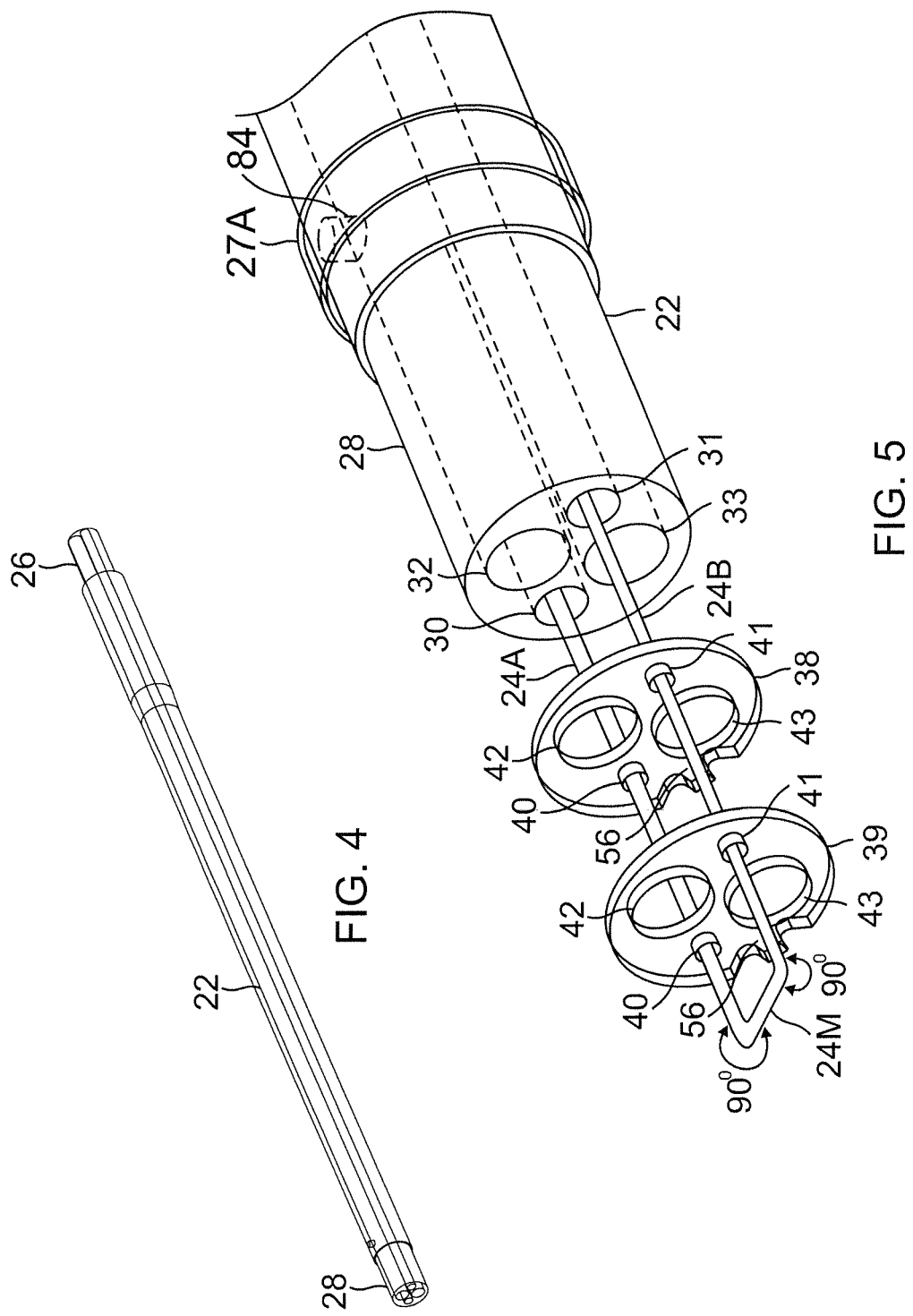

DOUBLE LOOP LASSO WITH SINGLE PULLER WIRE FOR BI-DIRECTIONAL ACTUATION

CROSS-REFERENCE TO RELATED APPLICATION

The present application is a Continuation under 35 U.S.C. § 120 of U.S. patent application Ser. No. 15/925,557, filed Mar. 19, 2018, issued as U.S. Pat. No. 10,485,610, which is a Continuation of U.S. patent application Ser. No. 15/144,705, filed May 2, 2016, issued as U.S. Pat. No. 9,918,791, which is a Continuation of U.S. patent application Ser. No. 14/733,833, filed Jun. 8, 2015, issued as U.S. Pat. No. 9,326,818, which is a Continuation of U.S. patent application Ser. No. 13/732,283, filed Dec. 31, 2012, issued as U.S. Pat. No. 9,050,010. The entire contents of these applications are incorporated by reference herein in their entirety.

FIELD OF THE INVENTION

The present invention relates to an improved ablation catheter that is particularly useful for mapping or ablating in a tubular region of or near the heart.

BACKGROUND OF THE INVENTION

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a distal assembly that is adapted to measure activity and/or ablate within a pulmonary vein, coronary sinus or other tubular structure about the inner circumference of the structure. One such distal assembly has a tubular structure comprising a generally circular main region generally transverse and distal to the catheter shaft and having an outer circumference of about 360 degrees and a generally straight distal region distal to the main region. The tubular structure comprises a non-conductive cover over at least the main region of the distal assembly. A support member having shape-memory is disposed within at least the main region of the mapping assembly. A plurality of electrode pairs, each comprising two ring electrodes, are carried by the generally circular main region of the distal assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the distal assembly. The catheter is maneuvered through movements that include deflection of a distal portion of the catheter so that the distal assembly is positioned at the tubular region in the heart chamber. The ability to control the exact position and orientation of the catheter and also the configuration of the distal assembly is critical and largely determines the usefulness of the catheter.

Deflection and steering of the catheter is typically accomplished by a control handle that houses deflection mechanism responsive to an actuator provided on the control handle. A puller wire extends through the catheter in a lumen along one side and the deflection mechanism draws on the puller wire proximally to deflect the catheter toward that side. Bi-directional deflection is accomplished by two opposing puller wires, each along one side of the catheter. By manipulating the actuator in one selected direction or another, the deflection mechanism acts on a selected puller wire to deflect the catheter along that side of the catheter. The distal end of each puller wire is typically anchored by means of a crimped ferrule soldered to a tip dome or a T-bar adhesive bonded to a diamond cut groove in a side wall of a tubing. However, these anchoring means can be offset from the lumens thus subject the puller wire to combined stresses of bending and shear along with tensile stresses. Moreover, tip deflection can also be skewed and off plane reducing predictability of desired deflection.

Another issue with catheters arises from free play and slippage between the support member of the distal assembly and the nonconductive cover which reduces the accuracy of the mapping and ablation procedures. Furthermore, the support member can also dislodge or detach from the catheter when the distal assembly is subjected to repeated and/or excessive contact forces. Additionally, repeated and/or excessive contact forces can also damage components, such as a location sensor, that are near where the support member is anchored to the catheter.

Accordingly, there is a desire for a catheter that provides bi-direction deflection in a manner that avoids bending and shearing stresses on the puller wires and a catheter that avoids skewing or off-plane deflection. There is also a desire for a catheter that minimizes micro-movements between the support member and the cover during mapping and ablation and a catheter with a distal assembly that is reliably mounted to the catheter.

SUMMARY OF THE INVENTION

The present invention is directed to a catheter having a distal assembly mounted on its distal end. The distal assembly has a generally circular main portion, having at least one loop, if not two loops with an outer loop and an inner loop, each of which carries a plurality of ring electrodes adapted for mapping and/or ablation. The generally-circular main portion is generally transverse to a longitudinal axis of the catheter. The loops of the generally-circular main portion may lie within one plane or one loop may be more distal than another loop to form a spiral or helical pattern.

In one embodiment, the catheter has an elongated tubular catheter body with at least one lumen, a deflectable intermediate section with at least two off-axis lumens, and a distal assembly with a tubular structure having a generally straight proximal region attached to the deflectable intermediate section and a generally circular main region generally transverse and distal to the proximal region. The distal assembly has an elongated rod-like support member with shape memory extending through the length of the distal assembly. An extruded non-conductive cover covers the support member which extends through a first lumen of the cover. The first lumen is sized to provide a tight or interference fit with the support member to minimize free play and micro-movements between the cover and the support member. Lead wires for electrodes carried on the distal assembly extend through a second lumen formed in the cover. The cover is constructed of a material that readily conforms to the shape and configuration of the support member without heat treatment.

In one embodiment, a single continuous puller wire extends through the catheter to effectuate bi-directional deflection of the deflectable section. The deflectable section has at least two off-axis lumens for the puller wire which is pre-bent into a U-shape, with a mid-portion and two proximal end portions. At a distal end of the deflectable intermediate section, the mid-portion straddles the two off-axis lumens, each of which receives a proximal end portion that extends toward the control handle. To reinforce the distal end of the deflectable section against compression forces when a proximal end portion of the puller wire is acted on for deflection, at least one washer is provided between the mid-portion and the distal end. The washer has at least two holes, each axially aligned with a respective off-axis lumen of the deflectable section. Each hole is centered relative to the respective lumen so that each proximal end portion of the puller wire extending through a washer hole and an off-axis lumen is generally parallel with the longitudinal axis of the catheter and thus subjected to tensile forces only with minimal shear. Advantageously, bi-directional deflection effectuated in this manner is more predictably on-plane with less skewing.

In one embodiment, the support member of the distal assembly is anchored at its proximal end in a connector section extending between the deflectable intermediate section and the distal assembly. The connector section has a central lumen filled with adhesive to form an adhesive volume in which a proximal end of the support member is anchored. To that end, a proximal end of the support member is flattened to provide a more planar form, with more bonding surface. The proximal end is also serrated to provide an irregular bonding surface. Accordingly, the proximal end potted in the adhesive resists rotational and axial movements that may otherwise loosen or detach the support member and the distal assembly from the catheter.

In one embodiment, the each proximal end portion of the puller wire is surrounded by a compression coil that is flexible but resists compression. Accordingly, a distal end of the compression coil defines a location for initiation of a deflection curvature when the puller wire is acted on by deflection mechanism in the control handle. By providing a first compression coil with a longer length and a second compression coil with a shorter length, each proximal end portion of the puller wire has a different deflection initiation location and hence a different deflection curvature to provide nonsymmetrical bi-directional deflection.

In one embodiment, a location sensor is potted in the adhesive volume of the connector section. The sensor has a housing that encloses at least one sensing coil. The housing is generally encased in a protective tubing which isolates the at least one sensing coil from the adhesive volume and protects it from torsional and/or axial tension/compression forces acting on the adhesive volume that may damage the sensor.

DESCRIPTION OF THE DRAWINGS

These and other features and advantages of the present invention will be better understood by reference to the following detailed description when considered in conjunction with the accompanying drawings wherein:

FIG. 3 is a perspective view of a deflectable intermediate section, a connector section, and a distal assembly of the catheter of FIG. 1.

FIG. 3A is an end cross-sectional view of the deflectable intermediate section of FIG. 3, taken along line A-A.

FIG. 3B is an end cross-sectional view of the connector section of FIG. 3, taken along B-B.

FIG. 4 is a perspective view of a multi-lumened tubing of the deflectable intermediate section of FIG. 3.

FIG. 5 is an exploded perspective view of a distal end of the tubing of FIG. 4, along with two washers and a puller wire.

DETAILED DESCRIPTION

Figure 1:
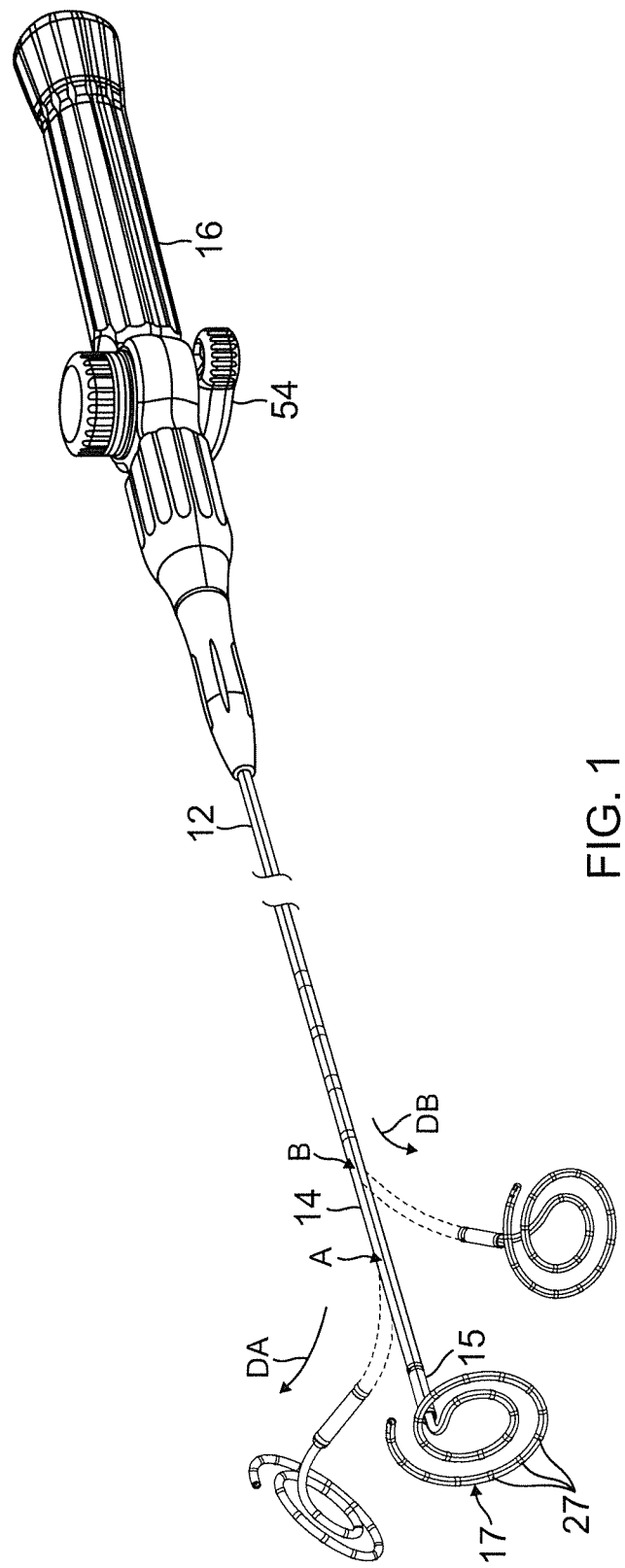
FIG. 1 is a perspective view of a catheter of the present invention, in accordance with one embodiment.

As shown in FIG. 1, a catheter 10 of the present invention comprises an elongated catheter body 12 having proximal and distal ends, a deflectable distal section 14 at the distal end of the catheter body, and a control handle 16 at the proximal end of the catheter body. The catheter also includes a distal assembly 17 that is mounted to a connector section 15 at a distal end of the distal section 14. The distal assembly carries a plurality of electrodes 27 adapted for mapping and/or ablation.

Figures 2, 2A:
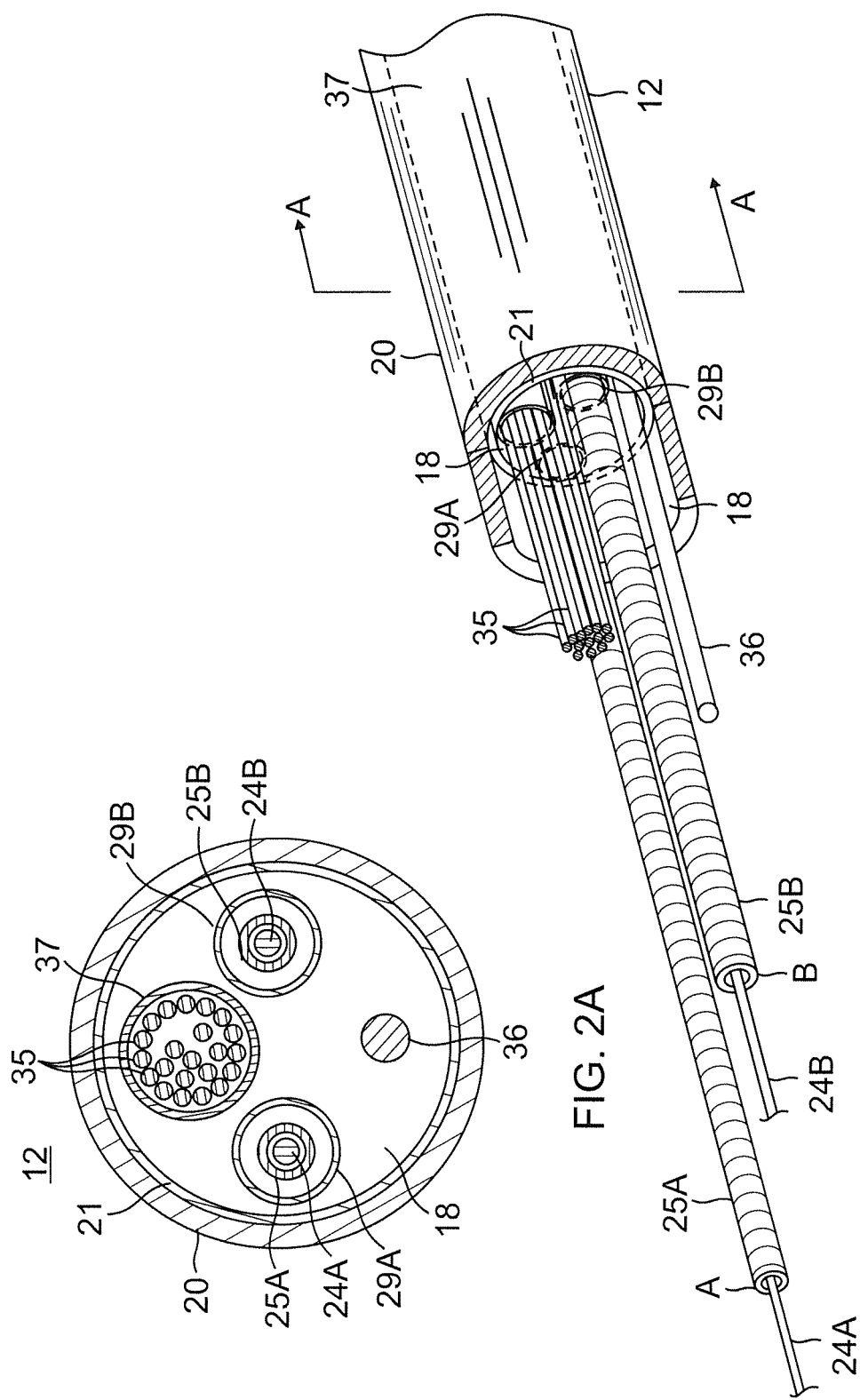
FIG. 2 is a perspective view of a catheter body of the catheter of the FIG. 1, with portions of an outer wall and a stiffener broken away.
FIG. 2A is an end cross-sectional view of the catheter body of FIG. 2, taken along line A-A.

With reference to FIGS. 2 and 2A, the catheter body 12 comprises an elongated tubular construction having a single, axial or central lumen 18. The catheter body 12 is flexible, i.e. bendable, but substantially non-compressible along its length. The catheter body 12 can be of any suitable construction and made of any suitable material. In the disclosed embodiment, the catheter body includes at least an outer wall 20 (e.g., of PEBAX or Pellethane). The outer wall 20 may include an imbedded braided mesh of stainless steel or the like to increase torsional stiffness of the catheter body 12 so that, when the control handle 16 is rotated, the catheter body 12 rotates in a corresponding manner.

The outer diameter of the catheter body 12 is not critical, but may be about 7 or 8 french. Likewise, the thickness of the outer wall 20 is not critical, but is thin enough so that the central lumen 18 can accommodate components including puller wires, multiple lead wires, cables and/or tubes. If desired the inner surface of the outer wall 20 may be lined with a stiffening tube (e.g., of polyimide) (not shown) to provide improved torsional stability and provide a reduction in shaft waviness during catheter deflection when puller wire tension places the catheter body in compression.

With reference to FIGS. 3 and 3A, the deflectable distal section 14 comprises a shorter section of tubing 22 having a plurality of lumens, including at least first and second off axis diametrically-opposing lumens 30 and 31, each for a puller wire. In the illustrated embodiment, there are also at least third and fourth off-axis lumens 32 and 33, the lumen 33 for a cable 36 connected to a position sensor 34, and the lumen 32 for lead wires 35 connected to the electrodes 27 carried on or near the distal assembly 17. Additional lumens may be provided as appropriate, such as for irrigation tubing to transport irrigation fluid to the distal assembly. The tubing 22 is made of a suitable non-toxic material that is preferably more flexible than the catheter body 12. One suitable material is for the tubing 22 is braided polyurethane, i.e. polyurethane with an embedded mesh of braided stainless steel or the like. The size of each lumen is not critical, but is sufficient to house the respective component, such as lead wires, puller wires, cables and tubings.

The useful length of the catheter body 12, i.e. that portion that can be inserted into the body excluding the distal assembly 17, can vary as desired. In one embodiment, the useful length ranges from about 110 cm to about 120 cm. The length of the distal section 14 is a relatively small portion of the useful length, and preferably ranges from about 3.5 cm to about 10 cm, more preferably from about 5 cm to about 6.5 cm.

To attach the catheter body 12 and the distal section 14, a proximal end of the tubing 22 of the distal section 14 comprises a smaller outer circumferential notch 26, as shown in FIG. 4, that receives an inner circumferential surface of a distal end of the outer wall 22 of the catheter body 12. The overlapping portions of the distal section 14 and catheter body 12 are attached by glue or the like. If desired, a spacer (not shown) can be located within the catheter body between the distal end of the stiffening tube (if provided) and the proximal end of the distal section. The spacer provides a transition in flexibility at the junction of the catheter body and distal section, which allows this junction to bend smoothly without folding or kinking. A catheter having such a spacer is described in U.S. Pat. No. 5,964,757, the disclosure of which is incorporated herein by reference.

As shown in FIG. 3, the connector section 15 has a short cylindrical member or tubing 23 with a central lumen 19 which houses the location sensor 34 and anchors a proximal end of the distal assembly 17. The tubing 23 may be constructed of any suitable material, for example, PEEK. To attach the distal section 14 and the connector section 15, a distal end of the tubing 22 of the deflectable section 14 comprises a smaller outer circumferential notch 28, as shown in FIG. 4, that receives an inner circumferential surface of a proximal end of the cylindrical member 23. The overlapping end of the tubings 22 and 23 are attached by glue or the like.

To effectuate deflection along the catheter body 12 for steering the catheter body 12 and the distal assembly 17, a puller wire 24 extends from the control handle 16 and through the entirety of the catheter body 12 (FIG. 2). In accordance with a feature of the present invention, the puller wire is a single continuous tensile member that provides bi-directional deflection, that is, deflection along two sides of the catheter in opposing directions within a plane defined by the first and second lumens 30 and 31 of the tubing 22 of the distal section 14, as shown in FIG. 1. As also shown in FIG. 5, the puller wire 24 has a first longitudinal proximal portion 24A extending through the lumen 30, a second longitudinal proximal portion 24B extending through the lumen 31, and a mid-short portion 24M that is formed between two opposing bends or corners with angles at about 90 degrees. The longitudinal portions 24A and 24B are parallel with a longitudinal axis of the catheter and the short portion 24M is generally perpendicular thereto as it straddles the lumens 30 and 31 at the distal end of the tubing 22. Both proximal ends of the puller wire 24 are anchored in the control handle 16 as understood by one of ordinary skill in the art. Deflection in one direction along one side of the catheter is enabled by a user's manipulation of an actuator 54 on the control handle 16 (FIG. 1) which draws one or the other long portion 24A or 24B proximally. In that regard, each long portion is surrounded by a respective compression coil 25A, 25B (FIG. 2) that extends from a proximal end of the catheter body 12 through the central lumen 18, into the respective lumen 30 or 31 of the distal section 14 (FIG. 3A) and terminates at predetermined distal locations A and B, respectively, (FIG. 1) along the length of the tubing 22 of the distal section 14. The puller wire 24 is made of any suitable metal, such as stainless steel or Nitinol. The puller wire 64 preferably has a diameter ranging from about 0.006 to about 0.010 inch.

Each compression coil 25A, 25B is made of any suitable metal, preferably stainless steel. The compression coil is tightly wound on itself to provide flexibility, i.e. bending, but to resist compression. The inner diameter of the compression coil is preferably slightly larger than the diameter of the puller wire. A Teflon® coating on the puller wire 24 allows it to slide freely within the compression coil. The outer surface of each compression coil 25A and 25B is covered by a flexible, non-conductive sheath 29A and 29B (FIG. 2), e.g. made of polyimide tubing.

Because each compression coil is flexible but resists compression, its distal end serves as a desired location for initiation of deflection of the respective puller wire. The location for initiation for each puller wire may be even with each other along the longitudinal axis of the catheter, or the location can be different for each puller wire or puller wire portion (used interchangeably herein). In the illustrated embodiment of FIGS. 1 and 2, both locations A and B are generally between the distal and proximal ends of the deflectable section 14, and the location A is more distal than the location B which results in the catheter having a smaller or tighter deflection DA on the side of longitudinal portion 24A with longer compression coil 25A relative to the side of longitudinal portion 24B with shorter compression coil 24A which has a larger or looser deflection DB. As shown in FIG. 1, the deflection DA has a smaller curve with defined radius and the deflection DB has a larger curve with defined radius.

The compression coils are anchored at their proximal end to the stiffener 21 of the catheter body 12 by proximal glue joint and at their respective distal end in the lumens 30 and 31 by distal glue joints. Both glue joints preferably comprise polyurethane glue or the like. The glue may be applied by means of a syringe or the like through a hole made in the tubings of the catheter body and the deflectable distal portion 14. Such a hole may be formed, for example, by a needle or the like that punctures the wall of the tubings which is heated sufficiently to form a permanent hole. The glue is then introduced through the hole to the outer surface of the compression coils and wicks around the outer circumference to form a glue joint about the entire circumference of each compression coil.

As another feature of the present invention, at least one puller wire strain relief compression washer 38 is provided at the distal end of the tubing 22 to anchor the mid-portion 24M. As best illustrated in FIG. 5, the washer 38 is formed with at least two through-holes 40 and 41 that are each respectively axially-aligned with centers of the first and second lumens 30 and 31 of the distal section 14. Diameter of each hole 40 and 41 can be up to about 14% larger than the cross-diameter of the puller wire. During deflection, one long puller wire portion 24A or 24B is under tension and the washer 38 is compressed against the soft elastomeric distal end of the tubing 22 of the distal portion 14 due to the puller wire tensile forces imparted by the deflection mechanism housed in the control handle 16. Because the washer holes 40 and 41 are in alignment with the lumens 30 and 31, force vectors on each longitudinal portion 24A and 24B are in direct alignment with the lumens 30 and 31 and the longitudinal portions 24A and 24B are subjected to only tensile stress loading during deflection. This feature provides better tip deflection characteristics and reduces skew and off-plan deflection associated with prior bi-directional deflection configurations. The washer 38 can be made of any suitable material, including stainless steel, nitinol or titanium.

The washer 38 may have a tab 56 at its outer circumferential edge. Washers are made in large quantities from a single acid etched sheet and thus the tab 56 is a feature used to secure the washers during the manufacturing process.

In the illustrated embodiment of FIGS. 3 and 5, a second puller wire strain relief compression washer 39 is provided immediately adjacent and distal of the washer 38. The washers 38 and 39 are generally identical in structure and configuration to each other. A single or any plurality of washers may be used to provide the desired optimal thickness to minimize or prevent deformation of the distal tip of the tubing 22 during deflection by the puller wire.

With reference back to FIG. 5, the single continuous puller wire is pre-bent with the two 90 degree bends to form the portions 24A, 24B and 24M. The longitudinal portions 24A and 24B are each trained into the holes 40 and 41 of the washers 38 and 39 and the lumens 30 and 31 of the tubing 22. The two 90 degree bends combined with a tight tolerance between the washer holes 40 and 41 relative to the cross-section or thickness of the puller wire lock the puller wire in place relative to the tubing 22 of the distal section 14 and keep it from deforming and slipping at the 90 degree bends at the washer when tension is applied via the actuator and deflection mechanism.

With reference to FIG. 3, the proximal end of the tubing 23 of the connector section 15 that slips over the distal end of the tubing 22 covers the washers 38 and 39 and is bonded to the distal notched end 28 of the tubing 22 by a flexible adhesive, such as a two-part polyurethane. The central lumen 19 of the tubing 23 of the connector section 15 is occupied by various components that are potted therein by a suitable adhesive volume 47, e.g., epoxy. In the illustrated embodiment, the potted components include a proximal end portion 58 of a support member 50 of the distal assembly 17, a nonconductive transition tubing 44 for the lead wires 35 for the electrodes 27 on the distal assembly 17, and the location sensor 34 which extends from a distal end of the sensor cable 36. The location sensor 34 includes at least one sensing coil and housing for the coil (both not shown). The housing in turn is advantageously encased in a heat shrink cover or tubing 45 (best seen in FIG. 3B) to isolate the coil from the adhesive 47. As such, any stresses transmitted into the adhesive volume 47 from torsional and/or axial tension/compression forces acting on the support member 50 are decoupled from the sensor 34 as the sensor is not directly bonded to the adhesive volume 47. The expansion coefficient of the adhesive-based sensor housing and the adhesive need not match in order to prevent stress cracking of the sensor housing.

The lead wires 35 connected to the electrodes 27 carried on the catheter 10 pass through the nonconductive tubing 37 which passes from the control handle 16, and through the central lumen 18 of the catheter body 12, as shown in FIGS. 2 and 2A. The lead wires 35 then pass through the third lumen 32 of the deflectable section 14, and through a third through-hole 43 formed in each of the washers 38 and 39. The lead wires 37 then pass through a nonconductive tubing 44, e.g., constructed of polyimide, that extends through the connector section 15. The tubing 44 has a proximal end that extends a short distance proximally of the proximal end of the connector section 15, and a distal end that is generally coterminous with the distal end of the connector section 15. The washer holes 43 are axially aligned with the lumen 33 of the deflectable distal portion 14.

The sensor cable 36 extends from a proximal end of the sensor 34 and passes through a fourth, off-axis through-hole 44 formed in the washers 38 and 39, through the fourth lumen 34 of the deflectable distal portion 15, through the central lumen 18 of the catheter body 12 and into the control handle 16. A nonconductive tubing 46 surrounds a portion of the sensor cable that extends through the connector section 15. The tubing 46, e.g., constructed of polyimide, has a proximal end that extends a short distance proximally of the proximal end of the connector section 15, and a distal end that abuts a proximal end of the sensor 34.

Figure 6:
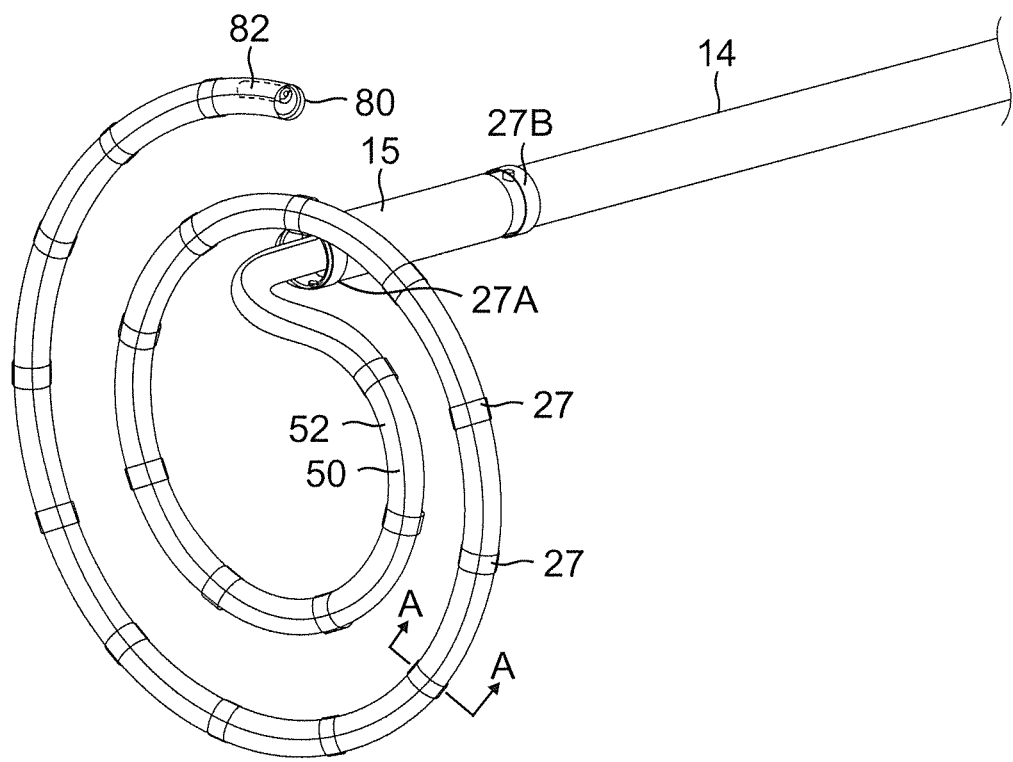
FIG. 6 a perspective view of the distal assembly, the connector section and a distal end of the deflectable intermediate section of FIG. 1.

As illustrated in FIGS. 3 and 6, the distal assembly 17 comprises a tubular structure that includes the support member 50, a non-conductive covering 52 and a plurality of ring electrodes 27. In the disclosed embodiment, the distal assembly 17 comprises a generally straight proximal portion 58 extending axially from the connector section 15, a generally straight portion 59 that is distal of the portion 58 and extending about 90 degrees therefrom, and a generally circular main region 60. Both portions 59 and 60 are generally transverse to the portion 58 and the connector section 15. As better seen in FIG. 7, the proximal region 58 (represented by X) is generally off-center of the generally circular main region 60. The proximal region 58 preferably has an exposed length, i.e. not contained within the connector section 15, ranging from about 3 mm to about 12 mm, more preferably about 3 mm to about 8 mm, still more preferably about 5 mm, but can vary as desired.

Figure 7:
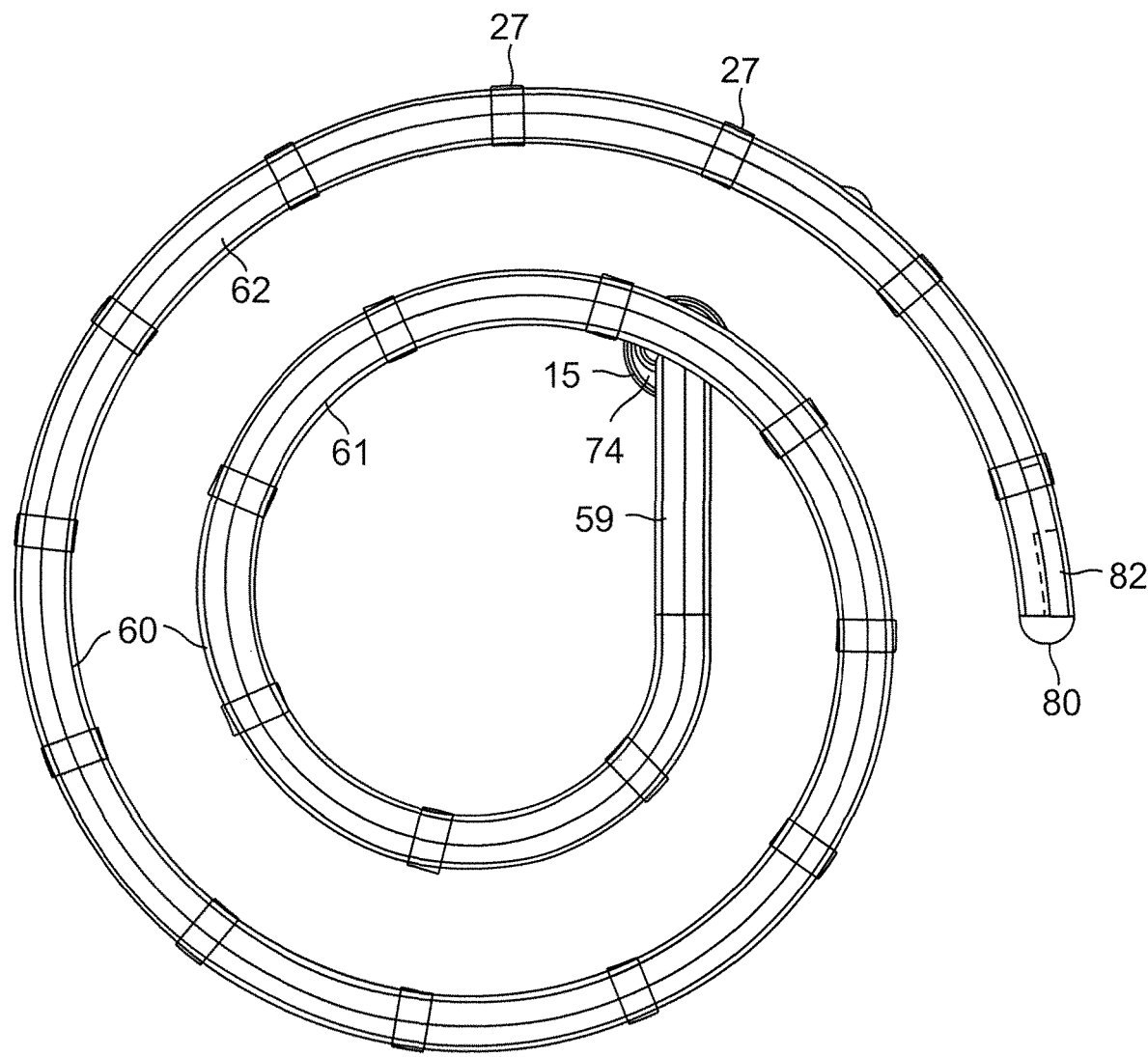
FIG. 7 is an end view of the distal assembly of FIG. 1.
Figure 8:
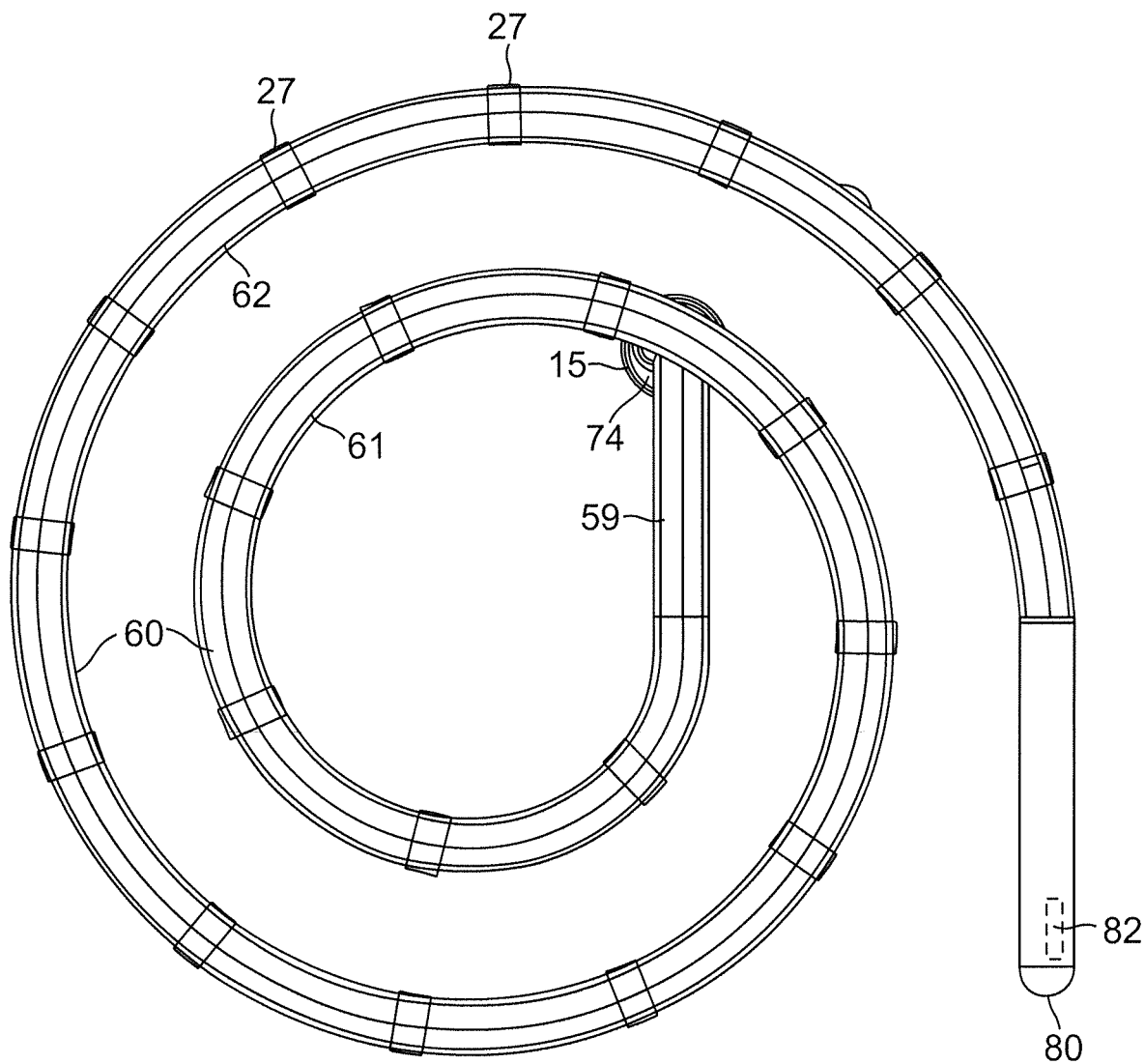
FIG. 8 is an end view of a distal assembly according to another embodiment.

As also shown in FIG. 7, the generally circular main region 60 forms at least a complete circle of 360 degrees, and more preferably, more than one loop or circle, e.g., two loops or circles with inner loop 61 and outer loop 62, of about 720 degrees so that it has, for example, a spiral or conical shape. The generally circular main region 60 is generally transverse to the catheter body 12 and the deflectable distal portion 14, and preferably forms an angle with the catheter body ranging from about 80 degrees to about 100 degrees, more preferably about 90 degrees. In the illustrated embodiment, both loops 61 and 62 generally lie within a common plane. However, it is understood that the loops 61 and 62 may be arranged such that one loop is more distal than the other loop such that the distal assembly has a generally spiral form. The generally circular main region 59 has an outer diameter preferably ranging from about 10 mm to about 40 mm, more preferably from about 10 mm to about 35 mm, still more preferably from about 12 mm to about 25 mm, even more preferably about 20 mm. The length of the exposed distal assembly 17 (when laid out straight) from its proximal end to the distal tip, including the regions 58, 59 and 60 ranges from about 2.2-6.2", more preferably about 3.6-5.4", and still more preferably about 4.2-4.9". In an alternative embodiment, the distal assembly 17 further comprises a generally straight distal region 64 that extends substantially tangentially from the generally circular main region 60, as shown in FIG. 8. The region 64 may have a length ranging from about 2.0 mm to about 18.0 mm, more preferably about 4.0 mm and 10.0 mm.

As shown in FIG. 3, the support rod or member 50 is elongated and extends through at least the entire length of the distal assembly 17 to provide its shape and configuration. The support member is made of a material having shape-memory, i.e. that can be straightened or bent out of its original shape upon exertion of a force and is capable of substantially returning to its original shape upon removal of the force. A suitable material for the support member is a nickel/titanium alloy. Such alloys typically comprise about 55% nickel and 45% titanium, but may comprise from about 54% to about 57% nickel with the balance being titanium. A suitable nickel/titanium alloy is nitinol, which has excellent shape memory, together with ductility, strength, corrosion resistance, electrical resistivity and temperature stability.

The support member 50 has a proximal end 70 that is proximal of the distal assembly 17. The proximal end is received and anchored in the adhesive volume of the connector section 15. In accordance with another feature of the present invention, a proximal portion of the proximal end 70 of the support member 50 is flattened and serrated with an uneven surface, e.g., a waffle or toothed surface, with raised and recessed regions to provide more bonding surface that is irregular for an adhesive bond joint that is equal or stronger than the torsional yield strength of a puller wire with a round cross-section. Changes to the cross-section configuration (e.g., from a round form into a more elliptical or rectangular form) and surface texture (e.g., from a generally smooth surface to a rough or uneven surfaces) at the proximal end 70 provide superior resistance to tensile pull out or rotation/spinning of the proximal end 70 of the support member 50 potted in the adhesive volume 47 in the connector section 15.

The extruded non-conductive cover 52 covering the support member 50 and other components of the distal assembly 17, including the lead wires 35 for the ring electrodes 27, can be made of any suitable material, and is preferably made of a biocompatible extruded plastic, e.g., polyurethane or PEBAX 25-35 D shore hardness. In accordance with another feature of the invention, the cover 52 is formed with at least two lumens 53 and 54, with the support member 50 extending through the lumen 53 and the lead wires 35 extending through the lumen 54. The lumen 53 for the support member 50 may be off-axis and on the side of the inner circumference of the generally circular region 60 so that the support member can better support the curvature of the region 60. The lumen 53 and its diameter are also particularly sized for a tight or frictional fit around the support member 50 to minimize or prevent free-play and micro-movements between the support member 50 and cover 52 during mapping or ablation procedure. The plastic material of the cover 52 advantageously conforms to the shape of the support member 50 without requiring heat treatment. It provides mechanical barrier and electrical isolation between the lead wires 35 and the support member 50. The cover 52 extends from a distal tip end of the distal assembly 17 to near the distal end of the connector section 15 which is sealed by a dome 74 constructed of a suitable biocompatible material, such as polyurethane. A distal tip end of the distal assembly 17 is sealed by a second dome 80 constructed of a suitable biocompatible material, such as polyurethane, to form an atraumatic tip end for the distal assembly. A distal end of the support member is surrounded by a short tubing 82, e.g., constructed of polyimide, to bond and anchor the dome 80. The material forming the dome 80 may be injected down inside the lumen of the tubing 82 and behind the tubing 82 to prevent the dome 80 from detaching.

The distal assembly 17 carries a series of electrodes 27, including ring electrodes, on the cover 52. The ring electrodes may be arranged equidistance apart from each other, or in closely-spaced pairs. As used herein, the term "ring electrode pair" refers to a pair of ring electrodes that are arranged closer to each other than they are to the other adjacent ring electrodes. Preferably the distance between two electrodes 27 of an electrode pair is less than about 3 mm, more preferably less than about 2 mm, still more preferably from about 0.5 mm to about 1.5 mm. The number of electrode can vary as desired, and preferably ranges from about 12 to 28 ring electrodes, more preferably about 20 ring electrodes.

In one embodiment, the width of each electrode is generally identical with the exception of the most distal ring electrode which has a greater width. The wider ring electrode provides a visual signal to the user of the location of the distal tip end when the catheter is being viewed under fluoroscopy. Specifically, because the mapping assembly is generally circular, it can be difficult for the user to determine which electrodes are placed at a particular location in the heart. By having one ring electrode, such as the most distal ring electrode, sized differently from the other ring electrodes, the user has a reference point when viewing the catheter under fluoroscopy.

Regardless of the size and number of the ring electrodes, the electrode pairs are preferably approximately evenly spaced around the generally circular main region 60. The closely-spaced electrode pairs allow for more accurate detection of near field pulmonary vein potential versus far field atrial signals, which is very important when trying to treat atrial fibrillation. Specifically, the near field pulmonary vein potentials are very small signals whereas the atria, located very close to the pulmonary vein, provides much larger signals. Accordingly, even when the distal assembly is placed in the pulmonary vein for mapping, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium by the electrical signal. However, it is understood that the ring electrodes may be configured to function in either uni-polar or bi-polar capacity.

Multiple ring electrodes, for example, about two to 26, and more preferably about 20, are mounted on the non-conductive cover 52 of the generally circular main region 60 of the ablation assembly 17. Such ring electrodes might be desirable, for example, for mapping and/or ablation. A description of a catheter including such ring electrodes is described in U.S. patent application Ser. No. 09/551,467, entitled "Catheter Having Mapping Assembly," the entire disclosure of which is incorporated herein by reference. If desired, additional ring electrodes (not shown) could be mounted elsewhere along the distal assembly 17 and/or distal portion 14. In the illustrated embodiment of FIG. 6, a ring electrode 27A is mounted at or near the distal end of the connector section 15, and a ring electrode 27B is mounted at or near the proximal end of the connector section 15.

Figure 6A:
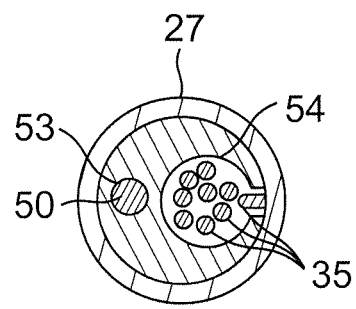
FIG. 6A is an end cross-sectional view of the distal assembly of FIG. 6, taken along line A-A.

Connection of a lead wire to the ring electrode is preferably accomplished by first making a hole through a wall of the tubing on which the ring electrode is mounted. A lead wire is then drawn through the hole. The end of the lead wire is then stripped of any coating and soldered or welded to the underside of the ring electrode, which is then slid into position over the hole and fixed in place with polyurethane glue or the like. Accordingly, for each ring electrode 27 carried on the distal assembly 17, a respective hole 85 (see FIG. 6A) is made through the wall of the cover 52 which communicates with the lumen 54 through which the respective lead wire 35 extends. For the ring electrodes 27A and 27B carried proximally of the distal assembly 17, their lead wires 40 extends through the lumen 33 alongside the sensor cable 36. For ring electrode 27B, a hole 87 (not shown) is made through the wall of the tubing 23 which communicates with the central lumen 19 of the connector section 15 through the respective lead wire extends. For the ring electrode 27A, a hole 84 (FIG. 3A) is made through the wall of the tubing 22 of the deflectable section 14 which communicates with the lumen 32 through which the respective lead wire extends. Proximal end of each electrode lead wire 35 is connected to a suitable connector (not shown) at the proximal end of the control handle 16. The connector is connected to a suitable source of ablation energy (not shown), e.g., radio frequency (RF) energy.

In use, a suitable guiding sheath is inserted into the patient with its distal end positioned at a desired location for mapping and/or ablation. An example of a suitable guiding sheath for use in connection with the present invention is the Preface™ Braided Guiding Sheath, commercially available from Biosense Webster, Inc. (Diamond Bar, Calif.). The distal end of the sheath is guided into an area of interest, for example, one of the atria of the patient's heart. A catheter in accordance with the present invention is fed through the guiding sheath until its distal end extends out of the distal end of the guiding sheath. As the catheter is fed through the guiding sheath, the distal assembly 17 is straightened to fit through the sheath. Once the distal end of the catheter is positioned at the desired location, the guiding sheath is pulled proximally, allowing the deflectable distal portion 14 and the distal assembly 17 to extend outside the sheath, and the distal assembly 17 returns to its original shape. The distal assembly 17 is then inserted into a pulmonary vein or other tubular region (such as the coronary sinus, superior vena cava, or inferior vena cava) so that the outer circumference of each loop of the generally circular main region 60 of the assembly 17 is in contact with a respective circumference inside the tubular region.

The circular arrangement of the distal assembly 17 provides a stable mechanism for keeping the ring electrodes 27 in a desired location of the tubular region. The user can rotate the distal assembly 17 by rotating the control handle 16 to move the electrodes into contact with adjacent points along each circumference. The design of the distal assembly permits the user to more easily enable simultaneous contact of the ring electrodes with tissue along different circumferences of a tubular region, especially where the tubular region decreases in diameter or size with distance. The catheter of the present invention has a dual purpose design. Large areas of the heart wall can be mapped quickly (high density mapping) with most of the loops of the distal assembly in contact with the heart wall. If the outer diameter is sized correctly for the patient's anatomy, the catheter can also be used to map the pulmonary artery where the outer circumference of each loop is in contact with the artery wall.

As will be recognized by one skilled in the art, it is easier to turn the distal assembly in a direction such that the tip end is being pulled rather than pushed. For example, in the embodiments depicted herein, where the assembly 17 is formed in a counter-clockwise direction (when viewed distally from the control handle 16), it is preferable to turn the assembly in a clockwise direction. Accordingly, if desired, an arrow or other indicator (not shown) can be included on the handle or proximal end of the catheter body to indicate to the user the preferred direction for rotating the assembly 17 in the patient's body.

Suitable designs of catheters with bi-directional deflection, including suitable control handles for such embodiments, are described, for example, in U.S. Pat. Nos. 6,123,699, 6,171,277, 6,183,435, 6,183,463, 6,198,974, 6,210,407, and 6,267,746, the entire disclosures of which are incorporated herein by reference.

Alternatively, a second puller wire (not shown) can be included to vary or tighten the diameter or size of the generally circular region 60 of the distal assembly 17. Such an arrangement is generally described in U.S. Pat. No. 5,626,136, the disclosure of which is incorporated herein by reference. The above-referenced control handles could be used to manipulate the second puller wire.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. It is understood that the drawings are not necessarily to scale and that any feature of any embodiment may be incorporated in addition to or in place of any other feature of any other embodiment.

Accordingly, the foregoing description should not be read as pertaining only to the precise structures described and illustrated in the accompanying drawings, but rather should be read consistent with and as support to the following claims which are to have their fullest and fairest scope.

What is claimed is:

1. A catheter comprising:
   a catheter body including at least three lumens extending therethrough;
   an intermediate section attached to the catheter body, the intermediate section including a first off-axis lumen, a second off-axis lumen, and a third off-axis lumen such that the first off-axis lumen, the second off-axis lumen, and the third off-axis lumen are each aligned with a respective one of the at least three lumens of the catheter body;
   a washer disposed at a distal end of the intermediate section, the washer including a first washer lumen, a second washer lumen, and a third washer lumen;
   a single puller wire including a first proximal portion extending through the first off-axis lumen and the first washer lumen, a second proximal portion extending through the second off-axis lumen and the second washer lumen, and a mid-portion disposed transversely to the first proximal portion and the second proximal portion; and
   a plurality of lead wires extending through the third off-axis lumen and the third washer lumen.

2. The catheter of claim 1, in which the mid-portion of the single puller wire is disposed distal to the washer.

3. The catheter of claim 2, in which the distal end of the intermediate section comprises a connector section.

4. The catheter of claim 3, further comprising a distal assembly connected to the intermediate section by the connector section.

5. The catheter of claim 4, in which the washer is disposed in the connector section.

6. The catheter of claim 5, further comprising a position sensor disposed in the connector section.

7. The catheter of claim 6, in which the intermediate section further comprises a fourth off-axis lumen.

8. The catheter of claim 7, in which the washer further includes a fourth washer lumen.

9. The catheter of claim 8, further comprising a cable that extends through the fourth off-axis lumen and the fourth washer lumen and that is connected to the position sensor.

10. The catheter of claim 4, in which the distal assembly comprises a support member and a plurality of electrodes connected to the lead wires.

11. The catheter of claim 10, in which the support member comprises a shape memory material.

12. The catheter of claim 11, in which a proximal portion of the support member is anchored in the connector section.

13. The catheter of claim 12, in which the proximal portion of the support member is anchored in the connector section by an adhesive.

14. The catheter of claim 12, in which the proximal portion of the support member comprises serrations.

15. The catheter of claim 12, in which the proximal portion of the support member comprises raised regions and recessed regions.

16. The catheter of claim 12, in which the proximal portion of the support member comprises a toothed surface.

17. The catheter of claim 10, in which the distal assembly includes a circular region.

18. The catheter of claim 17, in which the circular region comprises at least a first loop.

19. The catheter of claim 18, in which the circular region further comprises a second loop.

20. The catheter of claim 18, in which the circular region comprises a spiral form.

* * * * *